(12) United States Patent
Ganapathy et al.

(10) Patent No.: US 12,171,617 B2
(45) Date of Patent: *Dec. 24, 2024

(54) SYSTEMS AND METHODS FOR DETECTING INTRACRANIAL PRESSURE AND VOLUME

(71) Applicants: Augusta University Research Institute, Inc., Augusta, GA (US); UtopiaCompression Corporation, Los Angeles, CA (US)

(72) Inventors: Priya Ganapathy, Sacramento, CA (US); Lakshmi Priya Rangaraju, Los Angeles, CA (US); Jacob Yadegar, Los Angeles, CA (US); Matthew Lyon, North Augusta, SC (US)

(73) Assignees: Augusta University Research Institute, Inc., Augusta, GA (US); UtopiaCompression Corporation, Los Angeles, CA (US)

( * ) Notice: Subject to any disclaimer, the term of this patent is extended or adjusted under 35 U.S.C. 154(b) by 5 days.

This patent is subject to a terminal disclaimer.

(21) Appl. No.: 17/224,236

(22) Filed: Apr. 7, 2021

(65) Prior Publication Data

US 2021/0251609 A1   Aug. 19, 2021

Related U.S. Application Data

(63) Continuation of application No. 14/789,509, filed on Jul. 1, 2015, now Pat. No. 10,987,088.

(Continued)

(51) Int. Cl.
*A61B 8/08* (2006.01)
*A61B 5/00* (2006.01)
(Continued)

(52) U.S. Cl.
CPC ............ *A61B 8/5207* (2013.01); *A61B 5/004* (2013.01); *A61B 5/031* (2013.01); *A61B 5/6821* (2013.01);
(Continued)

(58) Field of Classification Search
None
See application file for complete search history.

(56) References Cited

U.S. PATENT DOCUMENTS

| | | | |
|---|---|---|---|
| 6,387,051 B1 | 5/2002 | Ragauskas et al. | |
| 8,672,851 B1 * | 3/2014 | Quirk | A61B 8/4218 600/459 |

(Continued)

OTHER PUBLICATIONS

Hayreh, S. S. The Role of Optic Nerve Sheath Fenestration in Management of Anterior Ischemic Optic Neuropathy. Arch Ophthalmol. 1990. vol. 108, No. 8, pp. 1063-1064.

(Continued)

*Primary Examiner* — Jonathan Cwern
(74) *Attorney, Agent, or Firm* — Hinckley Allen & Snyder; Stephen Holmes (57) ABSTRACT

It has been discovered that even mild changes in cerebrospinal fluid (CSF) pressure or intracranial pressure (ICP) can be detected immediately as evidenced by distortions in the ONS surface structure. Further, the changes in the ONS persist after the CSF pressure has returned to normal. The stability of ONS distortions provides a means of detecting transient changes in brain pressure even when the use of the diagnostic ultrasound is delayed. One embodiment provides systems and methods for detecting or diagnosing brain injury by detecting distortions or deformations of the ONS, preferably using ultrasound.

21 Claims, 9 Drawing Sheets

Related U.S. Application Data (60) Provisional application No. 62/019,624, filed on Jul. 1, 2014.

(51) Int. Cl.
*A61B 5/03* (2006.01)
*A61B 6/50* (2024.01)
*A61B 8/00* (2006.01)
*A61B 8/10* (2006.01)
*A61B 8/14* (2006.01)
*A61B 5/055* (2006.01)
*A61B 6/00* (2024.01)
*A61B 6/03* (2006.01)

(52) U.S. Cl.
CPC ............ *A61B 6/501* (2013.01); *A61B 8/10* (2013.01); *A61B 8/4254* (2013.01); *A61B 8/483* (2013.01); *A61B 8/5223* (2013.01); A61B 5/0035 (2013.01); A61B 5/055 (2013.01); A61B 5/684 (2013.01); A61B 5/7282 (2013.01); A61B 6/032 (2013.01); A61B 6/037 (2013.01); A61B 6/506 (2013.01); A61B 6/5217 (2013.01); A61B 8/14 (2013.01); A61B 8/4494 (2013.01); A61B 8/463 (2013.01); A61B 8/488 (2013.01); A61B 8/5246 (2013.01); A61B 2576/02 (2013.01)

(56) References Cited

U.S. PATENT DOCUMENTS

| 10,987,088 B2* | 4/2021 | Lyon .................... A61B 6/501 |
| 2005/0054900 A1* | 3/2005 | Mawn .................... A61B 5/064 |
| | | 600/156 |
| 2010/0302507 A1* | 12/2010 | Desgroseilliers ........ A61B 3/14 |
| | | 351/246 |
| 2011/0137182 A1* | 6/2011 | Bellezza .............. A61B 5/4029 |
| | | 600/485 |
| 2011/0243415 A1* | 10/2011 | Yonezawa ................ G06T 7/12 |
| | | 382/131 |
| 2013/0150684 A1 | 6/2013 | Cooner |
| 2015/0051489 A1 | 2/2015 | Caluser et al. |
| 2020/0077906 A1 | 3/2020 | Lyon |

OTHER PUBLICATIONS

Killer, H.W., et al. Architecture of Arachnoid Trabeculae, Pillars, and Septa in the Subarachnoid Space of the Human Optic Nerve: Anatomy and Clinical Considerations. Br J Ophthalmol. 2003. vol. 87, No. 6, pp. 777-781.

Kimberly, H. H., et al. Correlation of Optic Nerve Sheath Diameter with Direct Measurement of Intracranial Pressure. Society for Academic Emergency Medicine. 2008. col. 15, No. 2, pp. 201-204.

* cited by examiner

SYSTEMS AND METHODS FOR DETECTING INTRACRANIAL PRESSURE AND VOLUME

CROSS REFERENCE TO RELATED APPLICATIONS

This application is a Continuation of U.S. Non-Provisional patent application Ser. No. 14/789,509 filed on Jul. 1, 2015, which claims benefit of and priority to U.S. Provisional Patent Application No. 62/019,624 filed on Jul. 1, 2014, both of which are incorporated by reference in their entirety.

FIELD OF THE INVENTION

The invention is generally directed to systems and methods for detecting brain injury in a subject.

BACKGROUND OF THE INVENTION

According to the Center of Disease Control and Prevention, an estimated 1.7 million people sustain a traumatic brain injury (TBI) annually (Faul M, Xu L, Wald M M, Coronado V G. *Traumatic Brain Injury in the United States: Emergency Department Visits, Hospitalizations and Deaths 2002-2006.* Atlanta (Ga.): Centers for Disease Control and Prevention, National Center for Injury Prevention and Control; 2010). Out of that 1.7 million people, 52,000 die, 275,000 are hospitalized, and 1.365 million are treated and released from an emergency department.

TBI is a spectrum, from mild, almost unnoticeable brain injury to severe brain injury that can lead to death or permanent disability. Mild TBI (MTBI) or concussion is one of the most common neurologic injuries, accounting for approximately 75% of all brain-injured people and leading to an annual cost of approximately $17 billion/year for treatment and rehabilitation (National Center for Injury Prevention and Control. *Report to Congress on Mild Traumatic Brain Injury in the United States: Steps to Prevent a Serious Public Health Problem.* Atlanta, Ga.: Centers for Disease Control and Prevention; 2003). As the name falsely implies, the symptoms of MTBI such as brief loss of consciousness, headache, confusion and dizziness often are transient and perceived as not serious or significant. However tissue changes, as a result of MTBI at the neuronal level can lead to significant, life-long impairment of a person's ability to function physically, cognitively, and psychologically.

As a result of no diagnosis or the false belief that the initial injury has resolved, individuals with MTBI are at increased risk for repeated head injury, because they often do not avoid the activity that caused the initial concussion. As a result of multiple episodes of MTBI, several syndromes can occur. Second Impact Syndrome (SIS) is damage to the brain that occurs when a second insult to the brain occurs soon after the initial MTBI episode. Because of the initial injury, physiological disturbances and disruption of the blood-brain barrier make the brain more susceptible to a second injury. The phenomena is characterized by release of oxygen free radicals and cellular inflammation leading to cerebral edema, hyperemia and subsequent increase in intracranial pressure (ICP) which in turn results in a disproportionate brain injury than would be expected from the second injury alone. Chronic Traumatic Brain Injury (CTBI) represents the cumulative, long-term neurological consequence of repetitive concussions (MTBI). CTBI results in varying degrees of motor, cognitive and behavioral impairments. The severe form of CTBI is referred to as dementia pugilistca and shares many characteristics with Alzheimer's disease. With limited treatment options for CTBI, identification and minimization of the frequency of the brain injury are key to prevention. The ability to definitively identify/diagnosis initial MTBI at the time of injury could significantly reduce the instances of repetitive brain damage.

There is no gold standard for the diagnosis of MTBI. Conventional imaging (Computed tomography and Magnetic Resonance Imaging) cannot detect these subtle changes in the neurons associated with MTBI. Neuropsychological testing is a specialized task-oriented evaluation of human brain behavior relationships. This testing relies upon the use of standardized testing methods to evaluate higher cognitive functioning as well as basic sensory-motor processes. Neuropsychological testing helps explain the functional impact resulting from a MTBI. However, neuropsychological testing requires specialized training to perform accurately, requires a substantial length of time to perform, and is not typically performed immediately after an injury. Other, newer, more sophisticated imaging technologies show promise in detecting MTBI such as Positron Emission Tomography (PET), Single Photon Emission Computerized Tomography (SPECT), Functional Magnetic Resonance Imaging (fMRI) and Diffuse Tensor Imaging (DTI). These methods are still in development and are not practical to use at the point of injury.

Other methods include the estimation of the pressure using a combination of transcranial Doppler (TCD) ultrasound equipment, which is designed to assess cerebral blood flow velocities and estimation of the optic nerve sheath diameter. Such techniques are taught for example in U.S. Patent Application Publication 2011/0137182 published Jun. 9, 2011 to Bellezza and Lai. Unfortunately, detection of optic nerve sheath diameter is difficult to perform automatically, and requires a skilled clinician to properly identify the appropriate nerve.

With limited diagnostic tools combined with the often subtle, mild symptoms, identification of this type of injury is difficult when suspected. Thus, there is a need for new systems and methods for detecting brain injury, in particular MTBI.

Therefore, it is an object of the invention to provide a portable or mobile device for detecting MTBI at the point of injury.

It is another object of the invention to provide systems and methods for the non-invasive detection or diagnosis of brain injury.

It is another object of the invention to provide systems and methods for the non-invasive detection of changes in volume within the cranium and brain size.

SUMMARY OF THE INVENTION

It has been discovered that even mild changes in cerebrospinal fluid (CSF) pressure or intracranial pressure (ICP) can be detected immediately as evidenced by distortions in the ONS surface structure. Further, the changes in the ONS persist after the CSF pressure has returned to normal. The stability of ONS distortions provides a means of detecting transient changes in brain pressure even when the use of the diagnostic ultrasound is delayed. One embodiment provides systems and methods for detecting or diagnosing brain injury by detecting distortions or deformations of the ONS, preferably using ultrasound. The distortions or deformations in the ONS correlate to the size of the pressure wave the brain suffers during a head injury. Because this technique can detect a wide range of pressure changes (less than 1 cm H$_2$O change or increase), it can be used to monitor for pressure waves that cause the full spectrum of traumatic brain injury (mild to severe). In a preferred embodiment, distortions or deformations of the ONS are used to detect mild brain injury.

Still another embodiment provides a method and system for detecting distortions or deformations in the ONS that are indicative of trauma that occurred in the past and are also indicative of an increased risk of suffering brain injury from future trauma to the head.

Another embodiment provides a method of estimating changes in volume within the cranium. Because pressure and volume are directly related in a closed system such as the subdural space, fluctuations in volume can be detected immediately, as with intracranial bleeding or cerebral spinal shunt malfunction, as well as chronically, as with brain atrophy.

DETAILED DESCRIPTION OF THE INVENTION

I. Detecting or Diagnosing Brain Injury

In the past decade, several clinical studies have reported use of ultrasound (US) to measure the optic nerve sheath (ONS) diameter (ONSD) in trauma patients and compared the results to direct intracranial pressure (ICP) measurements. Traditional measurement is made 3 mm posterior to the retina. Normal ONS diameter is <5 mm at a location of 3 mm posterior to the retina. ONS diameter greater than 5 mm at 3 mm posterior to the retina is indicative of elevated ICP. It has been discovered that changes in ONSD that are less than 5 mm can also be indicative of brain injury or the propensity to develop brain injury if the subject receives trauma to the head. In one embodiment, an ONS with deformations along the length of the ONS and/or increases in the volume of segments of the ONS along the length of the ONS is indicative of brain injury. The deformations or increases in volume of the ONS are relative to a healthy ONS that has not been injured. The changes in the contour and/or volume in segments of the ONS along the length of the ONS result from acute and chronic increases in ICP. Changes in the volume and/or deformations in the ONS are a more sensitive and predictive assay for diagnosing acute and chronic brain trauma as well as predicting the propensity of subsequent brain injury due to minor head injuries.

In the other embodiment the propensity or susceptibility for future traumatic brain injury (TBI) can be detected by looking at the change in the subjects baseline with maneuvers such as valsalva. These changes are due to the loss of protective ICP reflexes in the subject and as such we can gauge the susceptibility to future TBI.

The disclosed methods can be used to identify acute, chronic or dynamic changes in the surface of the ONS that indicate that a pressure wave has occurred, the magnitude of the pressure wave, and the resultant effect on the individual person's brain from the pressure wave. Parts of the surface of the optic nerve sheath will deform differently than other parts of the optic nerve sheath in response to the pressure wave. Thus, one method involves identifying surface changes in the optic nerve sheath to detect pressure and volume changes within the cranium that have occurred in the optic nerve sheath as well as within the cerebrospinal fluid. Individuals which need "more protection" from injury or who may be approaching the state of Chronic Traumatic Brain Injury can be identified with the disclosed methods. After a significant pressure wave (which may result in a concussion or traumatic brain injury) the ONS remains abnormal and will react abnormally to small pressure waves. The disclosed methods can be used to detect abnormal ONS dilation and surface changes in a subject which indicates that the subject has had a prior brain injury and that they are susceptible to further brain injury at smaller pressure (or forces) than if they had not had the prior injury.

Dynamic changes in the ONS can be detected using the disclosed methods. For example maneuvers such as strain, weight lifting, or valsalva technique can be used to induce a mild change in intracranial pressure of the subject. The disclosed methods can be used to see how the ONS surface deforms with the maneuvers. Changes in the ONS surface due to these maneuvers can be related this back to the subjects' susceptibility to future brain injury as well as monitoring for healing after a brain injury (return to play).

If the subject valsalvas and there is a substantial or abnormal change in the surface structure and volume, then the subject is susceptible for future concussions or TBI at a lower pressure or force of injury.

The ONS shape change only occurs with valsalva and other maneuvers when the individual has an impaired ability to limit changes in ICP. By detecting these shape changes while doing these maneuvers, the method can demonstrate loss of these reflexes which predispose the individual to further injury at lower levels of pressure or injury.

A. Detecting Volume Changes Within the Central Nervous System

The disclosed method can also determine if there are volume changes within the central nervous system. Since pressure and volume are proportional in a closed system such as the central nervous system, volume changes within the central nervous system can also be determined. This system can detect increases as well as decreases from the subject's normal volume. This volume change can be due to increases (e.g., Hydrocephalus) or decreases (e.g., CSF shunt malfunction) in the cerebrospinal fluid volume as well as increases (e.g., hemorrhage, hypertensive emergency) or decreases (e.g., ischemic stroke) in blood volume or increases (e.g., encephalitis) or decreases (brain atrophy) in brain size. Dynamic changes of the ONS surface and segmental volume can be compared to the subject's baseline measurements for small changes in volume. Large changes in volume can be determined by measurements of the ONS surface and segmental volume to normal baselines.

B. The Optic Nerve Sheath

Figure 1:
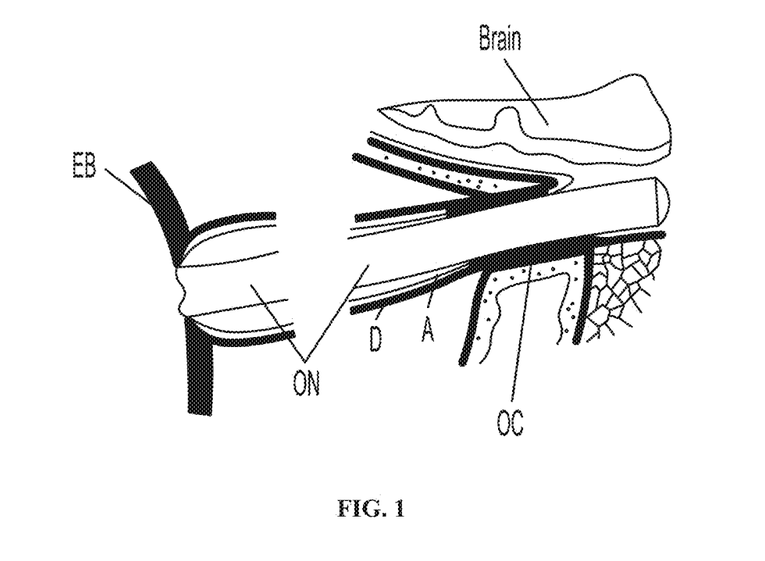
FIG. 1 is a schematic diagram showing various regions of the optic nerve sheath. A=arachnoid, D=dura, EB=eyeball, OC=optic canal, ON=optic nerve (Hayreh, Arch Ophthalmol., 108(8):1063-5 (1990)).
Figure 2:
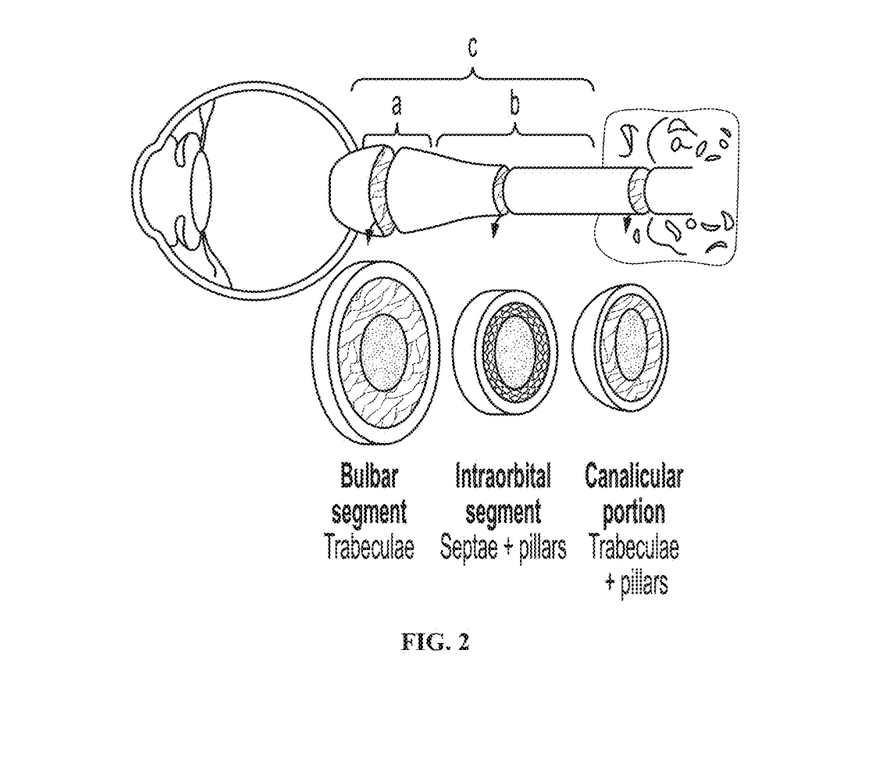
FIG. 2 is a schematic drawing of the optic nerve demonstrating the location of the (a) bulbar segment containing trabeculae, (b) mid-orbital segment containing septae and pillars, and (c) canalicular portion (containing pillars) (Killer et al., Br J Ophthalmol, 87:6 777-781 (2003)). Note that the type and density of fibers changes along the length of the sheath.
Figure 3A:
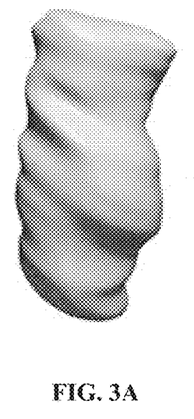
FIGS. 3A-3D are 3D ONS models constructed from 2D US scans of four out of five patients are shown as follows: Of the four, Subjects 1, 4 and 5 had elevated ICP (>20 mm Hg) at the measured instant. Subject 3 was dropped from the analysis due to heavy artifacts in the US scans that made reconstruction extremely difficult.
Figure 3B:
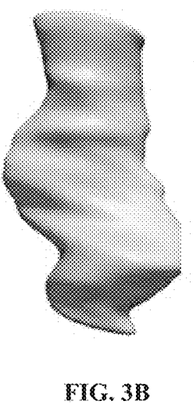
Figure 3C:
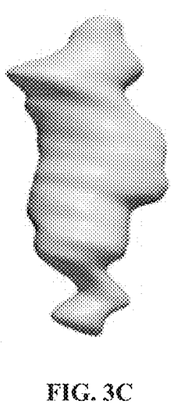
Figure 3D:
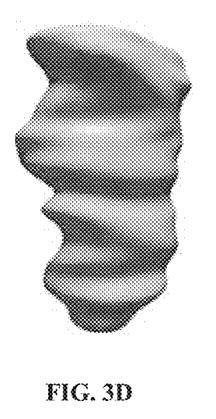

The ONS surrounds the optic nerve and contains CSF (FIG. 1). The ONS is composed of both distensible components and relatively ridged components (cables surrounded by balloon-like material (FIG. 2)). The more ridged structures (trabeculae) of the ONS are not affected by mild changes in pressure, while other portions (dura) dilate with small changes in pressure Because the components of the optic nerve expand at different rates with changes in the intracranial pressure (ICP), the diameter of the ONS along the length of the ONS changes with changes in the ICP.

A concussion results from a pressure wave that is transmitted through the skull to the brain. The insulting pressure wave is transient and results in transient elevations in the ICP (changes in the cerebrospinal fluid pressure). Since this is a dynamic process, medical diagnostic procedures are not focused on detection of this wave. However, it is this wave that, in mild TBI, leads to cellular disruption and an inflammatory response, as well as vessel disruption, loss of the blood brain barrier and los of the ICP moderating protective reflexes which leads to the sequela seen in mild TBI and concussion (post-concussive syndrome).

C. Fixed Point Measurements

One embodiment provides systems and methods of detecting brain injury by measuring the diameter of the ONS from several angles at a fixed-point centerline, for example 3 mm posterior to the retina. The radius of the ONS is measured from this point in all directions. In one embodiment, a length of 6 mm of the ONS is imaged to determine radius variability in the ONS. This method provides variability of the surface structure in addition to the overall volume. The surface variation is more sensitive for the chronic changes as well as the response to maneuvers such as Valsalva, straining, weight lifting, or head down position. The variation in the radius can be plotted along the length of the ONS to give better estimations as to chronicity of the injury as well as the severity.

Another embodiment provides a method in which the surface structure of the ONS is compared along the sheath (segment to segment) as well as to "normal" measurements i.e., measurement of uninjured ONS. Changes in the ONS shape (surface) and volume changes that occur with simple maneuvers discussed above such as valsalva and putting the patient in a head down position are indicative of abnormal subjects. These abnormal subjects are at a higher risk of brain injury if subjected to head trauma and are related to abnormal reflexes which protect the brain from sudden increases in ICP. Accordingly, this method can be used to determine whether an athlete has a concussion or other brain injury or is at a higher risk of brain injury if the athlete continues to participate in a sporting event. This method can also be used to monitor the healing process after a brain injury. Therefore it can be used to help determine when it is safe to return to sports activity (return to play).

Another embodiment provides methods for assessing a subject's ICP. A preferred method for assessing the subject's ICP includes obtaining the ONSD, preferably by non-invasive methods known in the art. Representative methods that can be used to determine the diameter of the ONS along the length of the ONS include, but are not limited to Positron Emission Tomography (PET), Single Photon Emission Computerized Tomography (SPECT), Functional Magnetic Resonance Imaging (fMRI), Diffuse Tensor Imaging (DTI), CT scan or MRI's, and ultrasound.

D. Cerebral Autoregulation

Still another embodiment provides systems and methods for detecting loss of the cerebral autoregulation mechanism. This mechanism is a protective mechanism and tries to maintain intracranial pressure by changing the blood flow into the brain. In one embodiment, the subject performs a valsalva maneuver (hold breath and bear down), and the ONS is imaged or ONSD are obtained along the length of the ONS or the segmental radius is determined along the length of the ONS. The ONS of subjects with abnormal auto regulation of the ICP would expand disproportionately to those who have not had a prior concussion and is indicative of a loss of the autoregulation of the pressure in the brain. Thus, subjects with deformations or distortions of the ONS, or having an ONS with increased radius variability along the length of the ONS relative to healthy, uninjured ONS have a loss of cerebral auto regulation. Such subjects are at a higher risk for suffering brain injury in response to head trauma relative to subjects with healthy, uninjured ONS. Further, the function of the autoregulation can be monitored over time. This can be used to indicate that the individual is able to return to sports play.

E. ONS Volume Measurements

Another method for detecting brain injury or increased ICP includes calculating the volume of segments of the ONS, preferably using ultrasound, wherein statistically or clinically significant changes in the volume of the ONS along the length of the ONS is indicative of brain injury or increased ICP or increased volume in the central nervous system. The segments can be of various dimensions including, but not limited to distance (millimeters) or volume (milliliters).

F. Three Dimensional Imaging of the ONS

Another embodiment provides a method for detecting or diagnosing brain injury or increased ICP by producing a three dimensional image of an ONS of a subject suspected of having brain injury and comparing the contour of the surface of the three dimensional image of the ONS with the contour of the three dimensional image of a healthy, uninjured ONS, wherein deformations in the ONS relative to the healthy, uninjured ONS is indicative of brain injury. The 3-dimensional image can be produced by stacking ONSDs obtained from images of the ONS. The 3-dimensional (3D) shape of the ONS can be used to detect subtle changes in the ICP.

Figure 10:
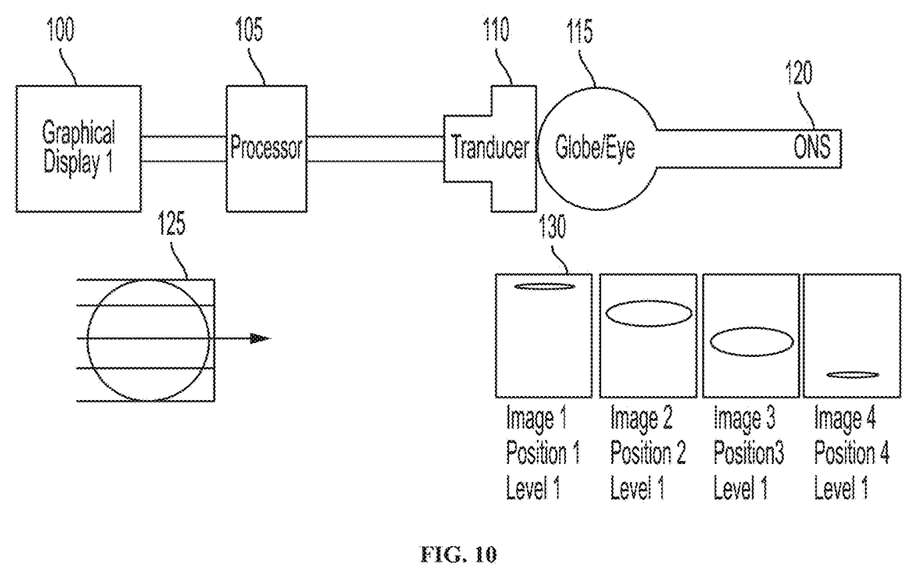
FIG. 10 is a schematic diagram of ultrasound transducer system for characterizing the ONS.

Referring to FIG. 10, the ultrasound transducer 110 contains a position sensor which can detect movement of the transducer 110. This can be any sensor that can detect movement of the ultrasound transducer such as a gyroscope. The operator would identify the edge of the ONS 120 using the ultrasound and position the ultrasound transducer 110 next to the eye 115. Then the operator would pan the transducer. The position sensor would correlate the movement of the transducer with the images 130 of the ONS 120 which are obtained automatically. The images 130 would be numbered and correlated one to another with a processor 105 using position data. 125 is a crosssection of the ONS showing four slices. The individual images would then be integrated into a single image. The boundary of the ONS would be automatically determined. The integrated image (3D representation of the ONS) would be displayed (Graphical Display 1 100). The depth of each image is adjusted based on time of pulse return.

Using the 3D model of the ONS one can visualize the surface of the ONS and detect subtle changes in the surface structure. These surface changes can be analyzed by measuring the diameter or area at different sites along the optic nerve sheath. Because the ONS has different components and reacts differently to mild changes in pressure, it is possible to detect small changes in the ICP. As the pressure becomes more severe, the whole sheath starts to become, or increasingly becomes dilated, similar to a balloon, as increasing pressure overcomes the ability of the rigid structures in the ONS to maintain the normal ONS shape and size.

The diameter of the ONS can be measured throughout the length of the ONS using the 3D model which improves the sensitivity and specificity over traditional 2D measurements. Since the ONS remains dilated for some period of time after a transient pressure wave, patients or athletes may be evaluated after an injury to detect if there was a change and how extensive the change was in the ICP. Further, if the ONS shape stays persistently dilated, then a structural change (i.e., intracranial bleeding) of the brain can be suspected (consistent with severe TBI) as the pressure will not return to the normal baseline level and the ONS will remain dilated. If the ONS shape changes during a maneuver such as valsalva or placing the patients head in a downward position, then the patient has propensity for brain injury with minor injuries which normally would not cause a brain injury.

Figure 11:
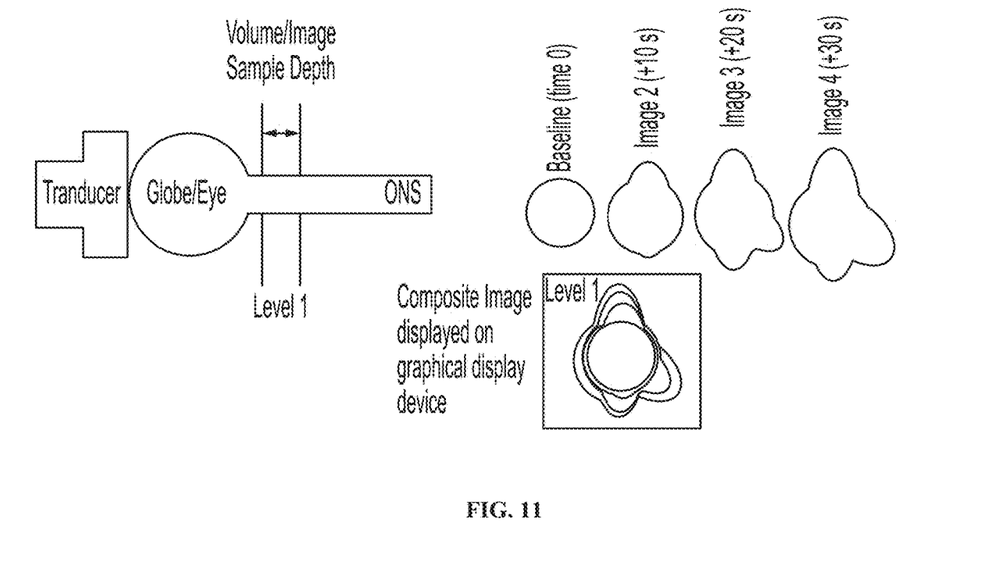
FIG. 11 is a schematic diagram showing composite imaging for maneuver analysis.

FIG. 11 shows the use of composite imaging for maneuver analysis. Volume/shape samples are taken at a fixed depth 140a posterior to the retina. Images 150 are obtained while the patient performs a maneuver which may increase intracranial pressure such as a valsalva maneuver. Images are taken in rapid repeated fashion (from 1 image per second to 1 image per 10 seconds). Since the ONS is not moving (but the edges are expanding) and since the interval of time between images 150 is known, the rate of change of the surface of the ONS can be calculated. A color coded image 160 (presented as grayscale image in FIG. 11) can be used to display the time sequence of images showing the dynamic changes in the ONS during the maneuver. This process can be repeated at different depths, along the ONS.

G. ONS Diameter Measurements

An alternative embodiment provides a line graph of ONSD along the length of the ONS, wherein statistically or clinically significant changes or both, for example increases or fluctuations in ONSD along the length of the ONS is indicative of brain injury or increased ICP. In a preferred embodiment, the increase in ONS is less than 5 mm and the ONS has deformations in the surface of the ONS and/or the ONS has increases in volume in segments along the length of the ONS. In yet another embodiment, at least one ONSD is taken 3 mm posterior to the retina.

Figure 13:
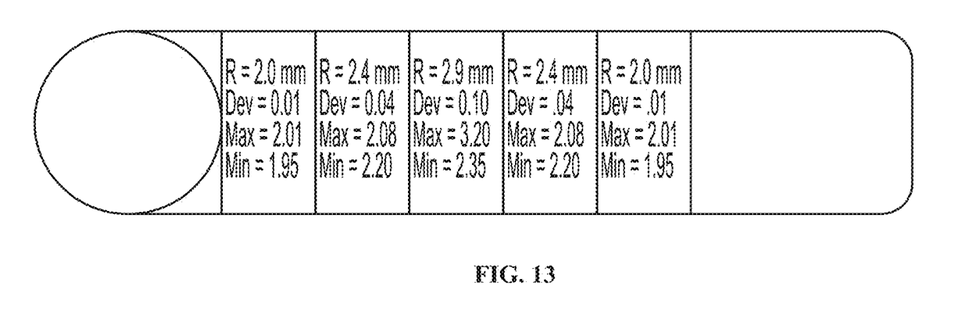
FIG. 13 is a graphical display of the variables for each segment of the optic nerve sheath that correspond to changes in the radius at that particular segment along the length of the ONS.
Figure 14:
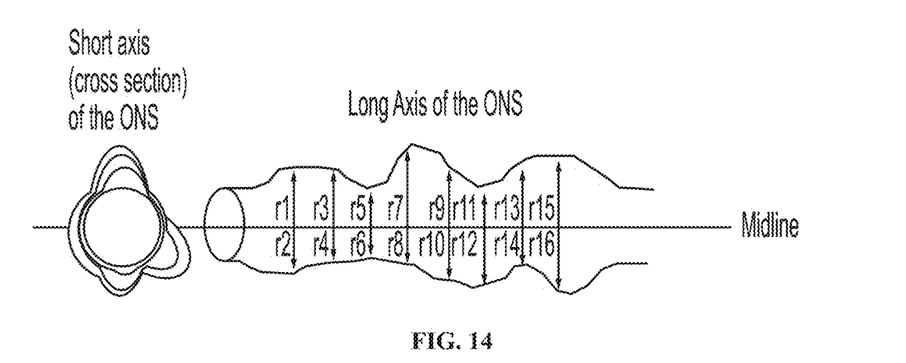
FIG. 14 is a schematic showing how radius variability can be a surrogate of surface variability.

FIG. 13 shows another graphical display of the variables for each segment (i.e., for 140a, 140b, 140c, or 140d) of the optic nerve sheath that correspond to changes in the radius at that particular segment along the length. The segment 140a can be color coded to match the severity of the changes in the surface deformations or the radius indicating abnormalities.

H. 3D Modeling

Three dimensional (3D) modeling of the optic nerve sheath by sonography correlates better with computed tomography (CT) and direct intracranial pressure (ICP) measurements than two dimensional measurements (2D), yielding a more accurate bedside imaging modality for traumatic brain injury. One embodiment provides a laptop-based ultrasound (US) system that detects traumatic brain injury though US imaging of the optic nerve anatomy.

One embodiment provides portable US systems integrated with affordable imaging/signal sensors capable of detecting TBI. New technology, using a combination of magnetic tracker sensors and traditional US technology, allows for 3D modeling of the ONS. In Example 1, data based on cadaveric as well as in patients with TBI demonstrate that 3D modeling of the ONS yield not only more accurate results than traditional 2D measurements of the ONS, but potentially, a more sensitive technique for injuries which are difficult to image with CT or Mill such as mild TBI (concussion) and shear type injuries to the brain.

One embodiment provides a portable US system which uses sensors and gyroscopes to give a relative position of the ultrasound transducer to the eye. The data can be segmented using an algorithm to detect the edge of the optic nerve sheath using a series of images taken as the transducer is panned from side to side. The depth of the image is correlated using standard US techniques based on time. Individual levels of the optic nerve sheath can be reconstructed using the positional and time data in conjunction with the edge detection algorithm.

One embodiment provides a portable ultrasound system which uses an annular array transducer to image the optic nerve sheath. The annular array sends out pulses and provides images of the optic nerve sheath along the axis of the optic nerve sheath. Depth can be determined using standard ultrasound based techniques based on the time from transmission of the signal to receiving the reflected signal. The boundary of the ONS is defined using an edge detection algorithm that differentiates the anechoic ONS from the hyperechoic surround structures. Each cross section of the ONS can be evaluated for surface (radial) irregularities as well as average, maximum, minimum radius distances and segmental volume. The individual cross sections can be combined to give surface reconstruction which can be analyzed for irregularities in the surface structure.

Figure 12:
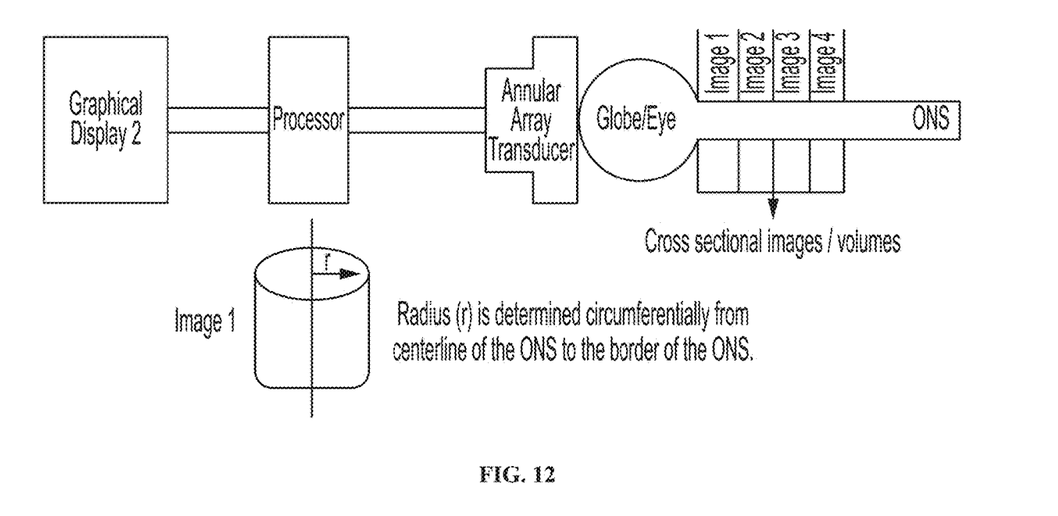
FIG. 12 is a schematic diagram showing cross section imaging of the ONS.

FIG. 12 is a schematic diagram showing cross section imaging of the ONS 120. Using an annular array transducer, cross sections of the ONS 120 are obtained. The Processor 105 would define the boundary of the ONS 120. The center of the ONS 120 is determined and the variance of the radius is measured. The maximum and minimum radius is also measured. This is done for each depth of the length (segments 140*a*, 140*b*, 140*c*, 140*d*, etc.) of the ONS 120 (Image 1, 2, 3, etc., collectively 170).

1. Image Acquisition

Using a SonoSite M-Turbo (SonoSite®, Bothell, Wash.), 2D US images of the ONS through a closed eye were recorded. The transducer position during image acquisition is correlated with the US images using a position and orientation tracker (MetriTrack™ MetriTrack, Inc., Hillside, Ill.). Mathematically, two coordinate systems are defined (a probe coordinate system, and a tracker coordinate system) in order to obtain the projection of a point in an image to its actual position in the world space. The position and time-corrected US images are then automatically registered and re-formatted to provide US data at any orthogonal or non-orthogonal slice planes.

2. 2D Pre-Processing

A single slice of the normal raw ONS image is filtered versions using median filtering and a delineated boundary of the ONS is obtained using mean shift algorithm. Once the ONS boundaries are delineated, a traditional edge-detector is used to segment out the region of interest.

3. 3D Modeling

Using a 2½ D approach for a surface reconstruction of the ONS from the segmented boundary slices, a surface representation of the ONS (3D model) was created. Contour slices can be manually delineated as well as the volume rendering of the ONS from these slices. A 3D model of the ONS was constructed from a set of 2D low resolution US images.

I. Length Variability as a Surrogate of Surface Variability

Each of the length measurements is taken from a fixed depth at midline of the ONS to the surface in all directions. These are labeled L1, L2, L3, etc. Each L (Length measurement) should be uniform in a normal subject (in each similar direction) with a normal contour ONS. L will increase and have increasing variability as the surface becomes irregular as happens with brain injury.

Comparison of the variability of the length measurements can be made over time or after an injury. The variability in the length can be used to monitor for acute injury, gauge the force the brain was subjected to during an injury, and to show how the patient is recovering from a brain injury.

The disclosed methods can also be used to follow for changes in CNS volume over time (brain atrophy) or used to gauge the amount of force the brain was subjected to during injury.

One embodiment provides a method for determining whether the patient is at risk for further brain injury by comparing baseline measurements to measurements made after maneuvers (i.e., Valsalva). If the length expands during valsalva, the patient has not recovered from their brain injury and the normal protective mechanisms (such as the cerebrospinal reflexes which maintain constant CSF pressure) has not been restored. The patient is at risk for further brain injury from subsequent minor head injuries.

J. Length Variability as a Surrogate of Surface Variability

Figure 15:
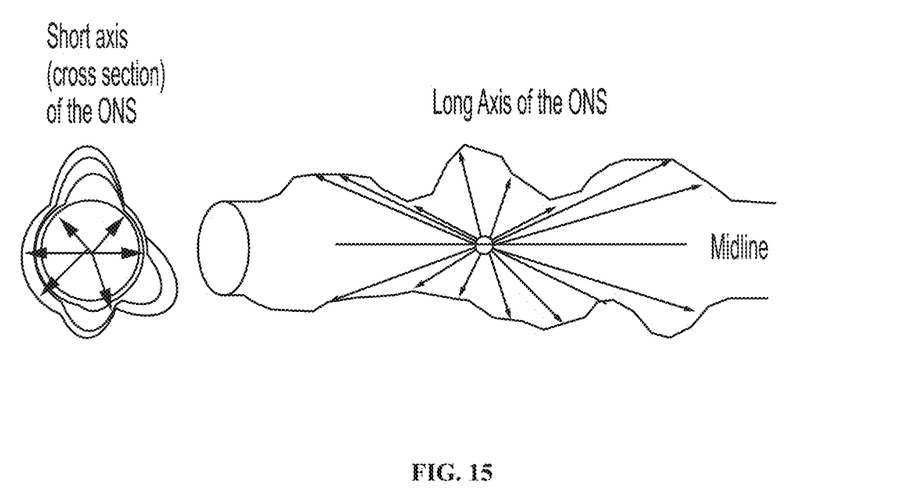
FIG. 15 is a schematic showing how length variability can be a surrogate of surface variability.

FIG. 15 shows how length variability can be a surrogate of surface variability. Each of the length measurements is taken from a fixed depth at midline of the ONS to the surface in all directions. These are labeled L1, L2, L3, etc. Each L (Length measurement) should be uniform in a normal subject (in each similar direction) with a normal contour ONS. L will increase and have increasing variability as the surface becomes irregular as happens with brain injury.

Comparison of the variability of the length measurements can be made over time or after an injury The variability in the length can be used to monitor for acute injury, gauge the force the brain was subjected to during an injury, and to show how the patient is recovering from a brain injury.

1) Screening Baseline Exam—Screening for minor brain injury or prior brain injury. Can also be used to follow changes in CNS volume over time (brain atrophy).
2) Compare Baseline Measurements to Measurements Immediate Post Injury—Use to gauge the amount of force the brain was subjected to during injury.
3) Compare Baseline Measurements to Measurements Made after Maneuvers (valsalva)—if the length expands during valsalva, the patient has not recovered from their brain injury and the normal protective mechanisms (such as the cerebrospinal reflexes which maintain constant CSF pressure) has not been restored. The patient is at risk for further brain injury from subsequent minor head injuries.

II. Systems and Devices

In a preferred embodiment, the disclosed systems and devices are portable and non-invasive. An exemplary device includes a component (e.g., a probe, such as a hand-held wand type probe) configured to obtain optic nerve sheath diameter and a component configured to, based on the optic nerve sheath diameter, produce an assessment of the subject's intracranial pressure.

The device may include two separate components (e.g., a separate probe for performing each of these tasks) or may include two components disposed inside a single probe, so that the user can use a single probe device to gather necessary information. In some embodiments, the device includes only a single component that acts to gather both pieces of information such that the device includes only a single component. A preferred device includes a single ultrasound probe gathers ONSD.

A suitable component may be an ultrasound transducer, an x-ray emitter, a magnetic resonance imager, a computed tomography scanner, optical coherence tomography scanner, and the like. Ultrasound transducers are considered especially suitable. The device may be a handheld instrument that includes a probe (e.g., an ultrasound probe) that is capable of obtaining optic nerve sheath diameter information. This may be obtained by collecting an ultrasound image of the eye under analysis, which image can then be interpreted by a user to arrive at an ONSD estimate. Existing ultrasound devices, such as those made by General Electric and by Multigon are considered suitable.

In some embodiments, the component is configured to gather image information from the subject's eye and calculate ONSD size based on the image in an automated fashion.

A component may be connected to a computer or other display so that the user may visualize the data being gathered by the component. The device may be configured to provide audio or visual instructions to the user to allow more precise positioning and operation of the device.

The device may also include a display screen, a printer, or other component to allow the user to visualize and analyze information collected by the device. The device may include a hard drive or other memory unity to allow recordation of data. The device may be connected to an information network, such as a hospital records system, so as to allow remote viewing and analysis/interpretation of information gathered by the device.

The device may also include a transmitter or radio system to as to allow the device to transmit information to a receiver. This enables a remote user—such as a physician located at a hospital—to view and interpret information that has been gathered in the field. The information-gathering probe may be wired or wirelessly connected to a computer or other device for data analysis. Alternatively, the probe may include an on-board analysis device or display device so as to allow the user to visualize or receive data on-site.

The components may be computer chips or hardware that reside on a single probe or other sensing device. Alternatively, the components may each be their own separate probe, where one probe is configured to collect ONSD information, and the other probe is configured to other physiological data from the subject. In such an embodiment, the device may include a central unit having two probes connected thereto.

The device may also include a central unit having a probe connected thereto. The devices used in the claimed methods can be configured to output a visual and/or audio warning for an operator to determine the proper medical intervention for a patient that is being screened for brain injury. In some embodiments, the probe itself may include a display device (e.g., a video screen or readout) so as to render the device portable.

Components that gather data by way of ultrasound are considered especially suitable. Physicians are familiar with ultrasound technology and it is one of the most widely used diagnostic tools in modern medicine. Compared to magnetic resonance imaging ("MRI") and computed tomography ("CT"), ultrasound technology is also relatively inexpensive and portable, although MRI and CT devices can take measurements of the ONS and have a higher resolution image than ultrasound, but are not portable.

Measurements on the eye are also ideally suited for ultrasound because the globe of the eye and the optic nerve sheath as they are fluid filled, which presents a suitable interface and medium for ultrasound to visualize the optic nerve sheath. ONSD measurements can be obtained using B-mode ultrasound imaging and blood velocity information can be obtained using Doppler ultrasound.

To perform these ultrasound measurements, an ultrasound probe of a suitable frequency is used. Lower frequency probes allow for deeper tissue penetration, while higher frequency probes allow for more imaging resolution.

ONSD measurements are taken 3 mm behind the eye or along the entire length of the ONS requiring a total tissue penetration of approximately 25 mm. The devices may feature imaging and Doppler capabilities built in, such that the operator can use the same probe and machine. Other devices may have only B-mode imaging (2D), the minimum required to make a ONSD measurement, with still other units having only Doppler ultrasound, which can only measure the velocity data. Ultrasound devices may operate at one or more frequencies. The device may also include a rechargeable battery, a removable memory device (e.g., a flash memory card), and the like.

The device may contain a magnetic tracking device, a gyroscope, or an annular array transducer to allow for correlation of position of the optic nerve sheath relative to transducer placement and motion.

Measurements can be performed by multifunctional bedside ultrasound units that are commonly found in trauma centers. One such unit is the GE Healthcare Logiq P5. By taking these measurements and using this method, a rapid assessment of ICP can be performed to aid the physician in determining if medical intervention is appropriate for a patient with a suspected head injury.

For a multifunctional unit, the operator takes an image of the desired target area, in this case the ONS, and then uses a distance measurement tool. Such a tool can be placing two crosshairs on an image and measuring the distance between the crosshairs.

The operator identifies the ONS and then manually marks the points and then use the software to make the measurement. This is similar process to measuring anatomical features on a fetus or the size and location of a tumor.

A device may be configured so as to automate the measurement by a combination of hardware mounts to ensure proper probe alignment and software algorithms to process the images to get the desired measurements. The process for obtaining Doppler velocity data is similar to the distance measurement. A 2D or 3D image of the target area is made by the operator.

The device may also be configured to collect ONSD information that outputs an ICP assessment score based on an algorithm as discussed above. The device may be configured to collected ONSD information in an automated fashion, e.g., by autofocus or by automated mage analysis techniques that locate the optic nerve and use edge detection or pattern recognition.

Such devices accomplish this collection by a combination of alignment tools and software algorithms to identify the proper target areas to collect data. The probe device may include a headband or other means for securing the probe to the head or face of the subject, so as to maintain the device in proper orientation for data gathering. A single probe may include separate components, one to measure ONSD information and additional physiological data. The components may gather information sequentially or simultaneously.

The components for obtaining ONSD could be a combination of an ultrasound transducer, and x-ray emitter, a magnetic resonance imaging (MRI) scanner, or a computed tomography (CT). The preferred component would be an ultrasound transducer configured such that both B-mode imaging and Doppler modalities are combined into one probe for a dedicated ICP assessment device. Such probes can interface with handheld computers, so the operator can scan a patient in the field using battery power and minimal physical footprint. ICP assessment can occur immediately after trauma, before patient transport and evacuation has to be arranged. Existing ultrasound platforms can be modified into an ICP assessment device that incorporates ONSD measurements.

These modifications can be done electronically in phased array, annular array and linear array ultrasound probes to collect both two-dimensional (B-mode) and continuous wave Doppler information. One illustrative electronic modification uses a time sharing arrangement in which the transducer rapidly switches back and forth from one type of examination to the other.

A physical modification may be done by mounting two ultrasound modalities together, for example a B-mode linear array of ultrasound transducers and a Doppler pulse wave piezoelectric crystal aligned so that the combined probe can target the same area of interest.

Also disclosed are systems for assessing a patient's ICP. These systems suitably include a first device configured to obtain, from a subject, optic nerve sheath diameter information; and the system being further configured to, based on the optic nerve sheath diameter produce an assessment of the subject's intracranial pressure.

The system may include a central processing unit that is connected to one or more probes. The central processing unit is suitably configured to assess the patient's ICP based on the data collected by the devices.

The system may be present in a kit form. The system may include gels or other media for facilitating probe engagement with the subject (e.g., a gel to facilitate transmission of ultrasound to the subject). The kit suitably includes instructions for use, as well as instructions for interpreting the output of the system. The kits may include carrying cases and the like to store and transport the system.

In one embodiment, the device captures images every few seconds while a subject, for example a sports player, performs a valsalva maneuver (hold breath and bear down). Patients with abnormal auto regulation of the ICP would expand disproportionately to those who have not had a prior concussion.

The device optionally includes lights or other means for aligning the transducer to image the optic nerve sheath of the subject. The subject can be directed to look at different lights on the device to induce strain on the optic nerve sheath which can be detected with the device.

EXAMPLES

Example 1: Cadaveric Trials

Materials and Methods

A cadaveric trial was chosen to study the speed at which the ONS dilates with increasing ICP. An invasive intracranial monitor was used to monitor the ICP as well as instill saline into the ventricle of the cadaver (increasing ICP) while simultaneous US scans of the ONS were performed to obtain 2D ONSD measurements.

Results

The ONS dilates near simultaneously with instillation of fluid into the intracranial space (ICS). The percent change in ONSD with change in ICP levels after saline instillation at different intervals. On an average, a 90% and 5% change in ICP and ONSD was recorded during the entire trial. Although the change in ONS dilation is simultaneous with ICP increase, the behavior of ONS dilation (varies from 4.2 mm to 5.3 mm) is less dynamic than change in ICP levels (4 cm/$H_2O$ to 34 cm/$H_2O$). Therefore, there is an impetus to develop sensitive and multiple biomarkers than a traditional 2D ONSD to accurately detect elevated ICP (onset of TBI).

Example 2: Human Trials

Materials and Methods

Data acquisition from 5 patients has been completed to date. Trauma patients, who were both sedated and on mechanical ventilation, with recent brain injuries were potential subjects in this protocol. ICP measurements were obtained from an invasively placed intracranial monitor. 2D US measurements of the ONS were obtained using a SonoSite Micromaxx US system (L38 10-5 MHz linear transducer). 3D modeling of the ONS was made using a combination of the L38 transducer coupled to a sensor, which maps the position and orientation of the transducer during the US exam. The position and time-corrected US images were then automatically re-formatted to provide US data at any orthogonal or non-orthogonal slice plane. Using a 2½ D approach for surface reconstruction, a 3D surface model of the ONS was generated from the segmented boundary slices. The ONSD measurements derived from a 2D image and from the 3D model of the ONS were compared to the direct ICP measurements.

Results

Figure 4:
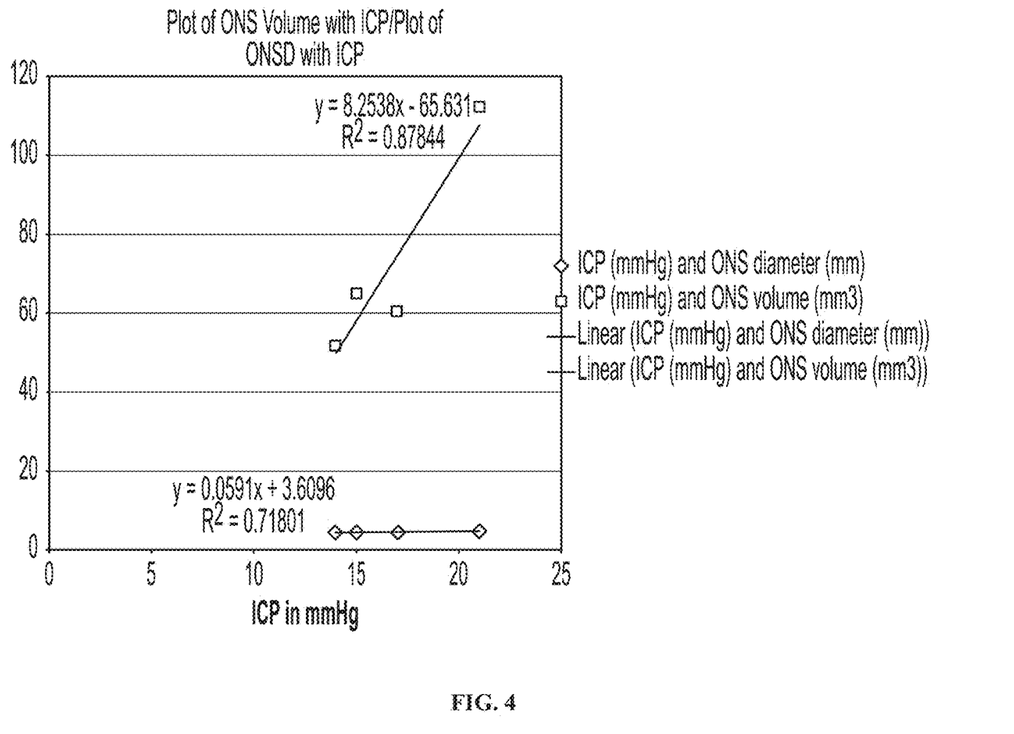
FIG. 4 is a line graph of ONS volume with ICP and a plot of ONSD with ICP.
Figure 5A:
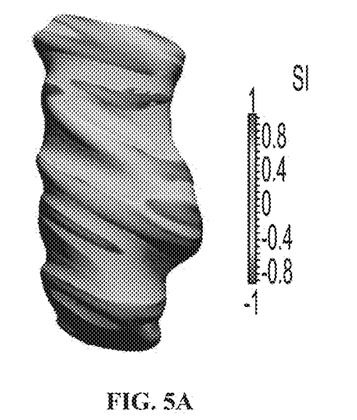
FIGS. 5A-5D are examples of figures for shape index (SI) and curviness overlay (CN) for subjects 1 and 4.
Figure 5B:
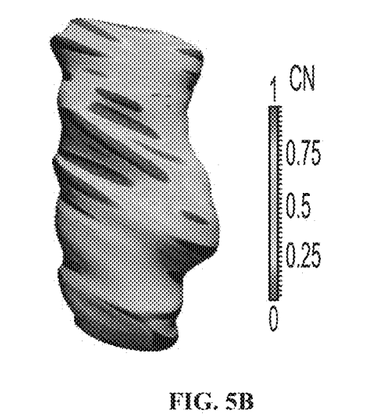
Figure 5C:
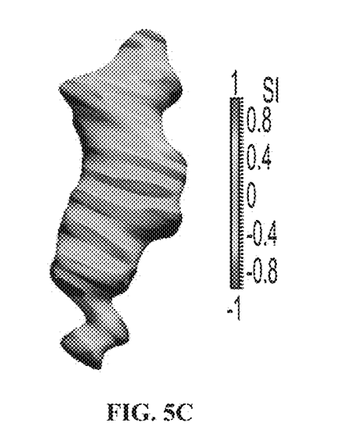
Figure 5D:
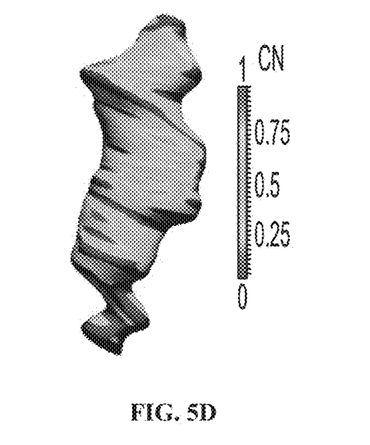

Preliminary analysis shows that the 3D ONS modeling is feasible in a clinical care setting yielding additional and more accurate information than the traditional 2D US measurements. 3D images of the ONS from TBI patients are shown in FIGS. 3A-3D. The average 2D ONSD measurements computed using the 3D ONS models correlate better to the invasive ICP levels measurements ($R^2$=0.92) than do the traditional, standard 2D ONSD measurements ($R^2$=0.35) (FIG. 4). Complex shape parameters such as shape index, Gaussian curvature, etc. can be derived from 3D models (FIGS. 5A-5D), possibly yielding additional clinical information that cannot be derived from traditional 2D US of the ONS. The correlation between conventional ONSD measurements and ICP values was reported as $R^2$=0.38. Average ONSD value for each subject (1, 2, 4 and 5) was computed from the 3D ONS models (i.e., averaging diameters along the ONS long axis) (FIGS. 3A-3D). Model-based ONSD measurements show high correlation ($R^2$=0.92) with ICP values. Here, a linear (first-order) model was fitted to the acquired data. The exact behavior of ONS dilation (linear or higher-order fit) with change in ICP can be predicted by increasing the sample dataset; increasing the number of samples will also improve strength of the correlation studies. These shape-based parameters show an improved correlation with ICP levels. Other non-invasive parameters including but not limited to cerebral blood flow, blood oxygenation, blood pressure, mean arterial pressure can also be measured and used to determine ICP of the subject.

Example 3: 3D Modeling of the Optic Nerve Sheath (ONS)

Materials and Methods

Figure 6A:
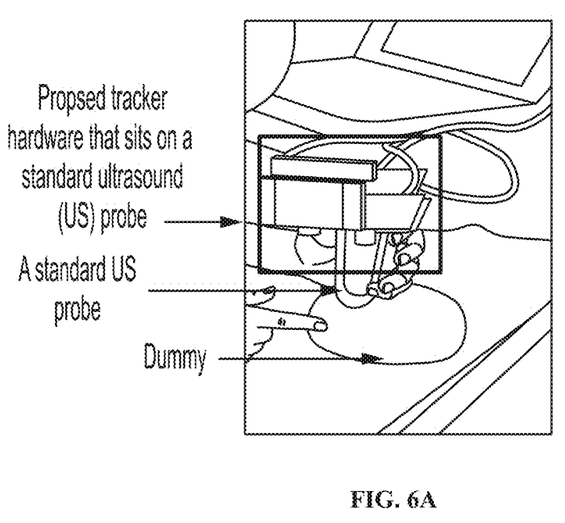
FIGS. 6A and 6B are photographs of an exemplary system for determining ICP in a subject.
Figure 6B:
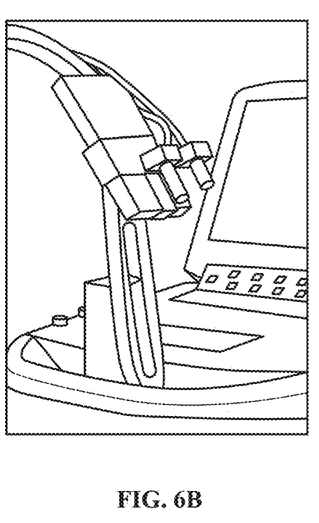

A 2D ultrasound transducer was used according to the manufacturer's instructions. The MetriTrack™ ultrasound system was used. This approach allows minimal-overhead 3D scanning with an innovative add-on device that is clipped onto standard ultra sound probes, near-instantaneous calibration, and has the potential to guide a variety of other image-guided interventions. Current version of CGM software version will perform "hands-off" 3D ultrasound reconstruction without system/operator interaction (FIGS. 6A and 6B). This probe tracking and reconstruction is performed with sensors entirely integrated into a clip-on bracket for handheld US probes (FIGS. 6A and 6B), with stereo cameras observing the environment (both on the patient and the surrounding background) and extract features that are salient enough to support probe trajectory reconstruction. Furthermore, in adverse conditions 3D environment surfaces can be generated to allow tracking. Either of these data sets is continuously registered frame-by-frame, and thus allowing the pairing of ultrasound images with poses, which in turn are used to reconstruct 3D US volumes. These volume scans (i.e., a series of 2D registered slices) are saved as DICOM images that are furtherer processed.

Patients

ONSD measurements were obtained from four patients diagnosed with severe traumatic brain injury.

Results

Using 2D ultrasound and transducer tracking technology, a 3 dimensional (3D) image of the optic nerve sheath was formed (FIGS. 3A-3D) by "stacking" ONSDs taken at locations along the length of the ONS. The data from patients with severe TBI have demonstrated a stronger correlation between the 3D derived measurements and the ICP than is found with the 2D measurements (FIG. 4).

Example 4: Porcine Studies

Materials and Methods

Using a porcine model, an epidural pressure monitor was placed in the epidural space of the tempo-parietal junction. Using a second incision on the contralateral temp-parietal junction a catheter with a balloon was placed in the epidural space. Saline was used to inflate the balloon on the catheter while simultaneous measurements were taken of the optic nerve sheath using 2D measurements (SonoSite Micromaxx US system, L38 10-5 MHz linear transducer). 3D modeling of the ONS was made using a combination of the L38 transducer coupled to a sensor, which maps the position and orientation of the transducer during the US exam. The position and time-corrected US images were then automatically re-formatted to provide US data at any orthogonal or non-orthogonal slice plane. Using a 2½ D approach for surface reconstruction, a 3D surface model of the ONS was generated from the segmented boundary slices. Volumes were calculated at pressure increases of 1 cm $H_2O$ as measured by the epidural monitor. After the ICP reached a maximum (when the cerebral perfusion pressure reached zero) the balloon was deflated retuning the ICP to baseline. The ultrasound measurements of the ONS continued until the 2D measurements reached the baseline diameter.

Results

Figure 7:
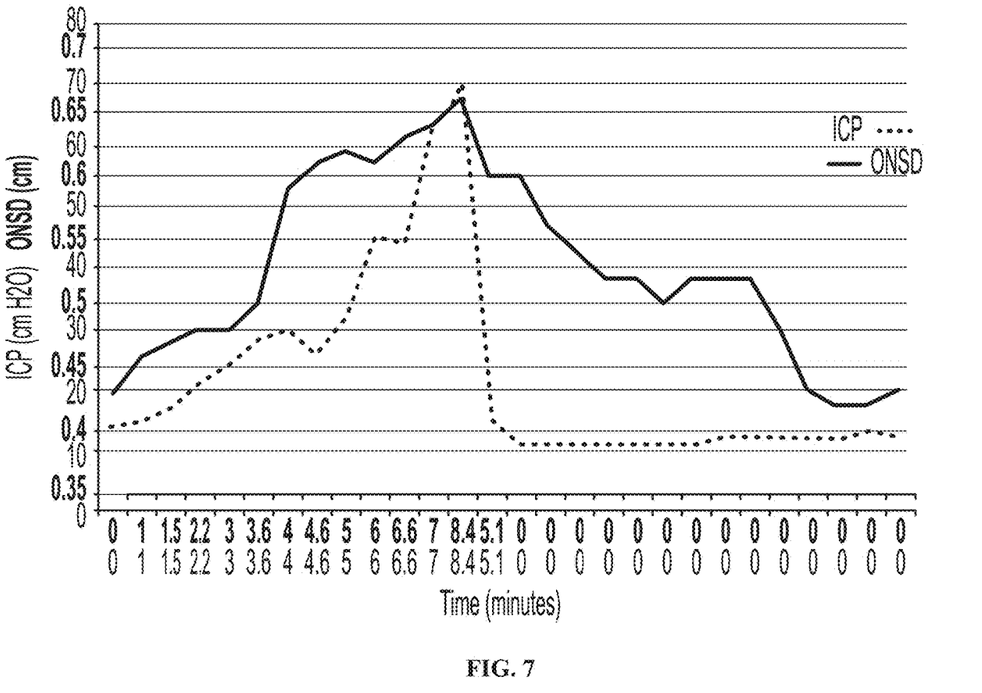
FIG. 7 is a line graph of ONSD (cm) or ICP (cm H$_2$O) versus time (minutes).
Figure 9:
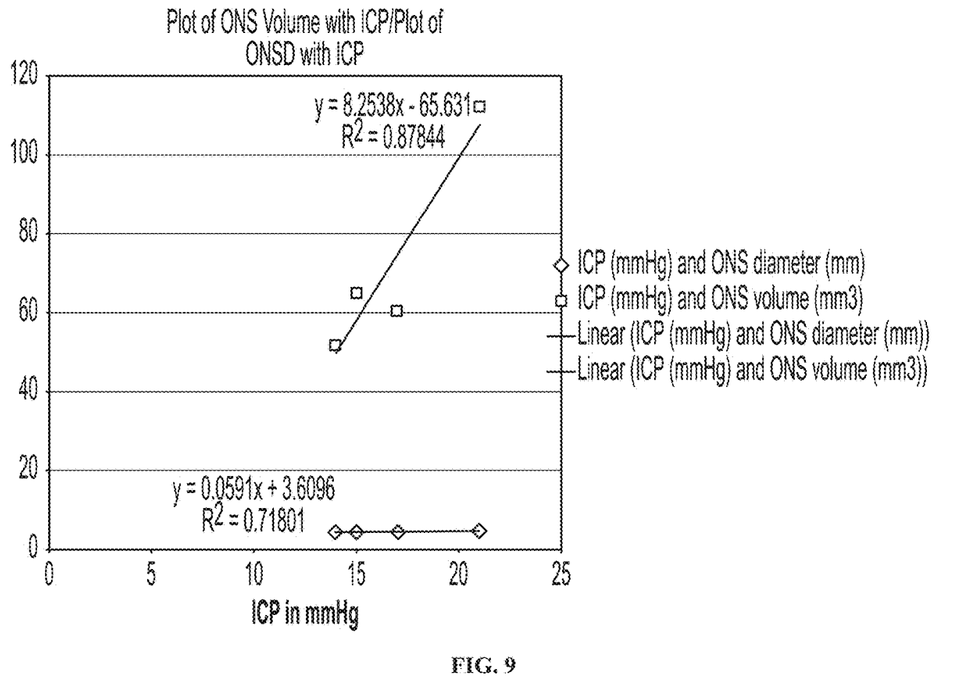
FIG. 9 is a graph of ONS volume (mm$^3$) versus intracranial pressure (mmHg) and ONS diameter (mm) versus intracranial pressure (mmHg). The ONS diameter changed very little with small changes in the ICP. However, ONS Volume varied dramatically with small changes in ICP.

Using a porcine model, the near linear, immediate relationship between the ONS diameter and the ICP was confirmed. This relationship remains until the Cerebral Perfusion Pressure (CPP) is near zero, at which there is a nonlinear relationship. By using a novel method of increasing the ICP, we were able to quickly decrease the ICP in our model to baseline. With this model, we were able to demonstrate with the rapid decrease in ICP (simulating a transient change in ICP), the ONS remained dilated for 30 minutes (FIG. 7). Note that the change in the ONS is approximately linear to the change in the ICP until the CPP is near zero. Also note that the ONS diameter after the ICP returns to baseline remains dilated for approximately 30 minutes. We also confirmed that the volume measurements of the 3D optic nerve sheath correlated linearly with small changes in ICP. The small changes in ICP were not measurable using the ONS diameter but volume measurement was highly sensitive to pressure changes. (FIG. 9).

Figure 8A:
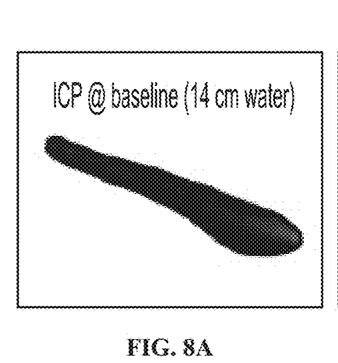
FIGS. 8A-8C are 3D ONS models at baseline and mild increases in ICP (14, 15, and 21 cm of water respectively).
Figure 8B:
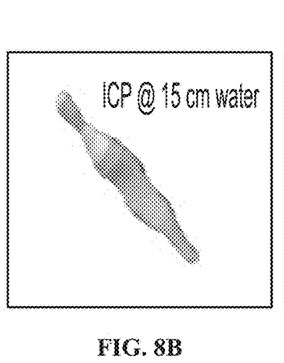
Figure 8C:
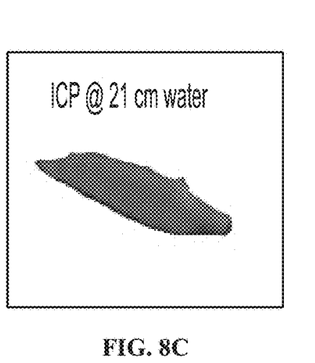

By surface mapping the changes in the 3D shape of the ONS, very mild changes in the ICP can be detected. At baseline in this model, the 3D ONS is linear and smooth (little variability in the cross sectional diameter along the ONS), like a tube or a pipe. As the ICP increases from approximately 14 to 20 cm water, the surface of the 3D ONS model becomes serpigenous (FIGS. 8a-8c). While the overall diameter of the ONS remains relatively unchanged (due to the rigid structures in the ONS) with mild changes in the ICP, the surface of the ONS changes drastically. By measuring the area variability at finite segments of the 3D ONS model, minor changes in the ICP can be detected (i.e., the diameter variability, along the ONS sheath, increases with increasing intracranial pressure in the mild ICP range). After an ICP greater than 20 (clinically elevated ICP), the ONS diameter is greater than 5 mm, our cut off for a moderately increased ICP.

We claim:

1. A method for detecting traumatic brain injury in a subject comprising the steps of:
    obtaining a plurality of images of the subject's Optic Nerve Sheath (ONS) along the length of the subject's ONS that extends outwardly behind the eye globe, the images being obtained at a tissue penetration depth of between 3 mm and 25 mm behind the eye globe;
    creating a three-dimensional (3D) model of a segment of the subject's ONS from said plurality of images, wherein the 3D model defines at least a surface contour and a volume of the 3D modeled segment;
    measuring from the 3D model the surface contour and the volume of the 3D modeled segment to determine a present state of the subject's ONS; and
    comparing the subject's present state measured ONS surface contour and volume to a baseline state 3D model surface contour and volume in order to identify present distortions of the subject's ONS surface contour and volume and to thereby characterize a present state of the subject's ONS and detect a current or recent traumatic brain injury.

2. The method of claim 1, wherein the step of obtaining a plurality of images comprises the steps of;
    obtaining a series of transverse ONS images;
    registering alignment of the transverse ONS images;
    reformatting the registered transverse ONS images to coronal slices;
    segmenting ONS contours from the coronal slices; and
    creating a 3D volumetric model from the segmented ONS contours.

3. The method of claim 2, wherein the surface contour of the 3D modeled segment of the ONS is measured as a variability of the surface contour of the 3D modeled segment of the ONS.

4. The method of claim 3, wherein variability of the surface contour is measured by measuring radial lengths from a centerline of the 3D modeled segment of the ONS to multiple points on an outer surface of the 3D modeled segment of the ONS.

5. The method of claim 3, wherein variability of the surface contour is measured by measuring lengths from a common point on a centerline of the 3D modeled segment of the ONS to multiple points on an outer surface of the 3D modeled segment of the ONS.

6. The method of claim 5 wherein the variability is measured over time.

7. The method of claim 3 further comprising the step of:
    providing a line graph of Optical Nerve Sheath Diameter (ONSD) measurements along a length of the 3D modeled segment of the ONS; and
    analyzing changes in ONSD, wherein changes in ONSD along a length of the 3D modeled segment of the ONS is indicative of brain injury.

8. The method of claim 3 wherein variability of the surface contour is measured by measuring length measurements from a fixed depth at a midline of the 3D modeled segment of the ONS to multiple points on the outer surface of the 3D modeled segment of the ONS.

9. The method of claim 8 wherein the variability is measured over time.

10. The method of claim 1, wherein the surface contour of the 3D modeled segment of the ONS is measured as a variability of the surface contour.

11. The method of claim 10, wherein variability of the surface contour of the 3D modeled segment of the ONS is measured by measuring radial lengths from a centerline of 3D modeled segment of the ONS to multiple points on an outer surface of the 3D modeled segment.

12. The method of claim 10, wherein variability of the surface contour is measured by measuring lengths from a common point on a centerline of the 3D modeled segment of the ONS to multiple points on an outer surface of the 3D modeled segment.

13. The method of claim 10 wherein the variability is measured over time.

14. The method of claim 10 wherein variability of the surface contour is measured by measuring length measurements from a fixed depth at a midline of the 3D modeled segment of the ONS to multiple points on the outer surface of the 3D modeled segment of the ONS.

15. The method of claim 14 wherein the variability is measured over time.

16. The method of claim 1 further comprising the step of:
providing a line graph of Optical Nerve Sheath Diameter (ONSD) measurements along a length of the 3D modeled segment of the ONS; and
analyzing changes in ONSD, wherein changes in ONSD along a length of the 3D modeled segment of ONS is indicative of brain injury.

17. The method of claim 1,
wherein the step of imaging comprises the steps of
obtaining a series of transverse 2D images with an imaging device, and
obtaining position and orientation data of the imaging device relative to the eye for each image as the imaging device is moved across the eye; and
wherein the step of creating said 3D model comprises the step of combining the obtained 2D images with said obtained position and orientation data to create said 3D model.

18. A method for detecting a traumatic brain injury in a subject comprising the steps of:
obtaining a plurality of images of the subject's Optic Nerve Sheath (ONS) along the length of the subject's ONS that extends outwardly behind the eye globe, the images being obtained at a tissue penetration depth of between 3 mm and 25 mm behind the eye globe;
creating a three-dimensional (3D) model of a segments of the subject's ONS from said plurality of images, wherein the 3D model defines at least a volume of the 3D modeled segment;
measuring from the 3D model the volume of the 3D modeled segment to determine a present state of the subject's ONS; and
comparing the subject's present state measured ONS volume to a baseline state 3D model volume in order to detect present distortions of the subject's ONS volume and to thereby characterize a present state of the subject's ONS and a detect a current or recent traumatic brain injury.

19. The method of claim 18,
wherein the step of imaging comprises the steps of
obtaining a series of transverse 2D images with an imaging device, and
obtaining position and orientation data of the imaging device relative to the eye for each image as the imaging device is moved across the eye; and
wherein the step of creating said 3D model comprises the step of combining the obtained 2D images with said obtained position and orientation data to create said 3D model.

20. A method for detecting a prior traumatic brain injury in a subject comprising the steps of:
obtaining a plurality of images of the subject's Optic Nerve Sheath (ONS) along the length of the subject's ONS that extends outwardly behind the eye globe, the images being obtained at a tissue penetration depth of between 3 mm and 25 mm behind the eye globe;
creating a three-dimensional (3D) model of a segment of the subjects' ONS from said plurality of images, wherein the 3D model defines at least a surface contour of the 3D modeled segment;
measuring from the 3D model the surface contour of the 3D modeled segment to determine a present state of the subject's ONS; and
comparing the subject's present state measured ONS surface contour to a baseline state 3D model surface contour in order to identify present distortions of the subject's ONS surface contour and to thereby characterize a present state of the subject's ONS and a detect a current or recent traumatic brain injury.

21. The method of claim 20,
wherein the step of imaging comprises the steps of
obtaining a series of transverse 2D images with an imaging device, and
obtaining position and orientation data of the imaging device relative to the eye for each image as the imaging device is moved across the eye; and
wherein the step of creating said 3D model comprises the step of combining the obtained 2D images with said obtained position and orientation data to create said 3D model.

* * * * *